(12) United States Patent
Kehres et al.

(10) Patent No.: US 8,002,773 B2
(45) Date of Patent: Aug. 23, 2011

(54) EXTERNAL FIXATOR

(75) Inventors: Clinton E. Kehres, Van Wert, OH (US); William Muhammad, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 672 days.

(21) Appl. No.: 12/214,168

(22) Filed: Jun. 17, 2008

(65) Prior Publication Data

US 2009/0312757 A1 Dec. 17, 2009

(51) Int. Cl.
*A61B 17/00* (2006.01)

(52) U.S. Cl. .......................................... 606/56; 606/54

(58) Field of Classification Search .............. 606/53–59, 606/252, 276, 277, 278, 260; 24/490, 494, 24/575; 175/414, 420.1; 73/818
See application file for complete search history.

(56) References Cited

U.S. PATENT DOCUMENTS

| | | | |
|---|---|---|---|
| 5,885,282 A * | 3/1999 | Szabo | 606/56 |
| 5,968,043 A * | 10/1999 | Ross et al. | 606/56 |
| 6,860,883 B2 * | 3/2005 | Janowski et al. | 606/56 |
| 7,226,449 B2 * | 6/2007 | Venturini et al. | 606/56 |
| 7,887,537 B2 * | 2/2011 | Ferrante et al. | 606/59 |
| 2003/0153910 A1 | 8/2003 | Janowski et al. | |

FOREIGN PATENT DOCUMENTS

WO WO 2007/024904 3/2007

* cited by examiner

*Primary Examiner* — Pedro Philogene
(74) *Attorney, Agent, or Firm* — Maginot, Moore & Beck

(57) ABSTRACT

An assembly includes a body, a plunger, a biasing member and a set screw. The body has a top surface, a bottom surface, and a polygonal drive surface interposed between the top surface and the bottom surface. The body has a first passageway extending from the top to the bottom surface, a second passageway extending from the polygonal drive surface to the first passageway, and a third passageway extending from the polygonal drive surface to the first or second passageway. The plunger has a channel that defines an interior surface having a threaded portion. The plunger moves within the second passageway. The biasing member biases the plunger toward a first plunger position. The set screw is movable within the third passageway between a first position in which the set screw inhibits movement and a second position in which the set screw allows movement of the plunger within the second passageway.

22 Claims, 11 Drawing Sheets

EXTERNAL FIXATOR

FIELD

This application relates generally to the field of orthopaedics, and more specifically to external fixators used in the reduction of long bones.

BACKGROUND

External fixation is a surgical treatment used to set bone fractures in which a cast would not allow proper alignment of the fracture. In this kind of reduction, holes are drilled into uninjured areas of bones around the fracture and special bolts or wires are screwed into the holes. Outside the body, a rod or a curved piece of metal with special joints joins the bolts to make a rigid support. External fixation is usually used when internal fixation is contraindicated often to treat open fractures, or as a temporary solution.

There are two main kinds of external fixators. One is known as mono-lateral fixation where the metal external structure is on one side of the limb. The other is circular fixation and in this case the metal structure is circular or an arch and surrounds the limb. Installation of the external fixator is performed in an operating room, normally under general anesthesia. Removal of the external frame and bolts can be done with no anesthesia in an office visit.

Circular fixation external fixators are often used for fractures of long bones that are weight bearing such as the femur and tibia. It is known that bearing weight through a fracture by walking on it, for example, with the added support of the external fixator frame actually helps fractures to heal. The benefit of weight bearing is due to a phenomenon known as Wolff's law. Wolff's law teaches that load on the fracture site under normal weight bearing promotes healing and avoids atrophy of the fracture site.

Circular fixation external fixators typically include two or more spaced apart rings. The rings surround the limb, for example the leg. Bone engaging pins are mounted onto the rings and extend inwardly through soft tissue including skin and muscle and engage the bone near the fracture site. The pins may engage only the outer cortical bone or engage cancellous bone as well and may extend entirely through the bone. The rings are spaced apart from each other by distractors in the form of externally threaded rods and internally threaded nuts.

These external fixators perform generally satisfactory, but are time consuming for the surgeon to assemble onto the patient. The threaded rods are very long and the threaded moving of the nuts along the rods requires many rotations of the nuts for each rod. Further there are three or more rods for each fixator. Also three or more rings may need to be adjusted. Further to obtain a tactile feel for distracting of the bone, nuts and rods with fine threads are preferred. All this threading of the nuts is very time consuming. This time consuming threading makes the surgery in which external fixators are installed slow and expensive and exposes the patient to risks associated with longer surgical procedures. Therefore, it would be advantageous to provide an improved external fixator.

SUMMARY

According to one embodiment of the present disclosure, there is provided an assembly including a body, a plunger, a biasing member, and a set screw. The body has a top surface, a bottom surface, and a polygonal drive surface interposed between the top surface and the bottom surface. The body has a first passageway extending from the top surface to the bottom surface, a second passageway extending from the polygonal drive surface to the first passageway, and a third passageway extending from the polygonal drive surface to the first or second passageway. The plunger has channel extending through the plunger that defines an interior surface having a threaded portion. The plunger moves within the second passageway between a first plunger position in which the threaded portion is located at a first location with respect to the body and a second plunger position in which the threaded portion is located at a second location with respect to the body. The biasing member biases the plunger toward the first plunger position. The set screw is movable within the third passageway between a first set screw position in which the set screw inhibits movement and a second set screw position in which the set screw allows movement of the plunger within the second passageway.

According to another embodiment of the present disclosure, there is provided an assembly including a body, a plunger, a biasing member, and a lock member. The body has a first surface, a second surface, and a third surface extending between the first surface and the second surface. The body defines a first passageway extending from the first surface to the second surface, a second passageway extending from the third surface to the first passageway, and a third passageway extending from the third surface to the first passageway or the second passageway. The plunger has a channel extending through the plunger that defines an interior surface having a threaded portion. The plunger is movable within the second passageway between a first plunger position in which the threaded portion is located at a first location with respect to the body and a second plunger position in which the threaded portion is located at a second location with respect to the body. The biasing member is configured to bias the plunger toward the first plunger position. The lock member is movable within the third passageway between a first lock member position in which the lock member inhibits movement of the plunger within the second passageway, and a second lock member position in which the lock member allows movement of the plunger within the second passageway.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

Corresponding reference characters indicate corresponding parts throughout the several views. Like reference characters tend to indicate like parts throughout the several views.

DETAILED DESCRIPTION OF THE PREFERRED EMBODIMENTS

Figure 1:
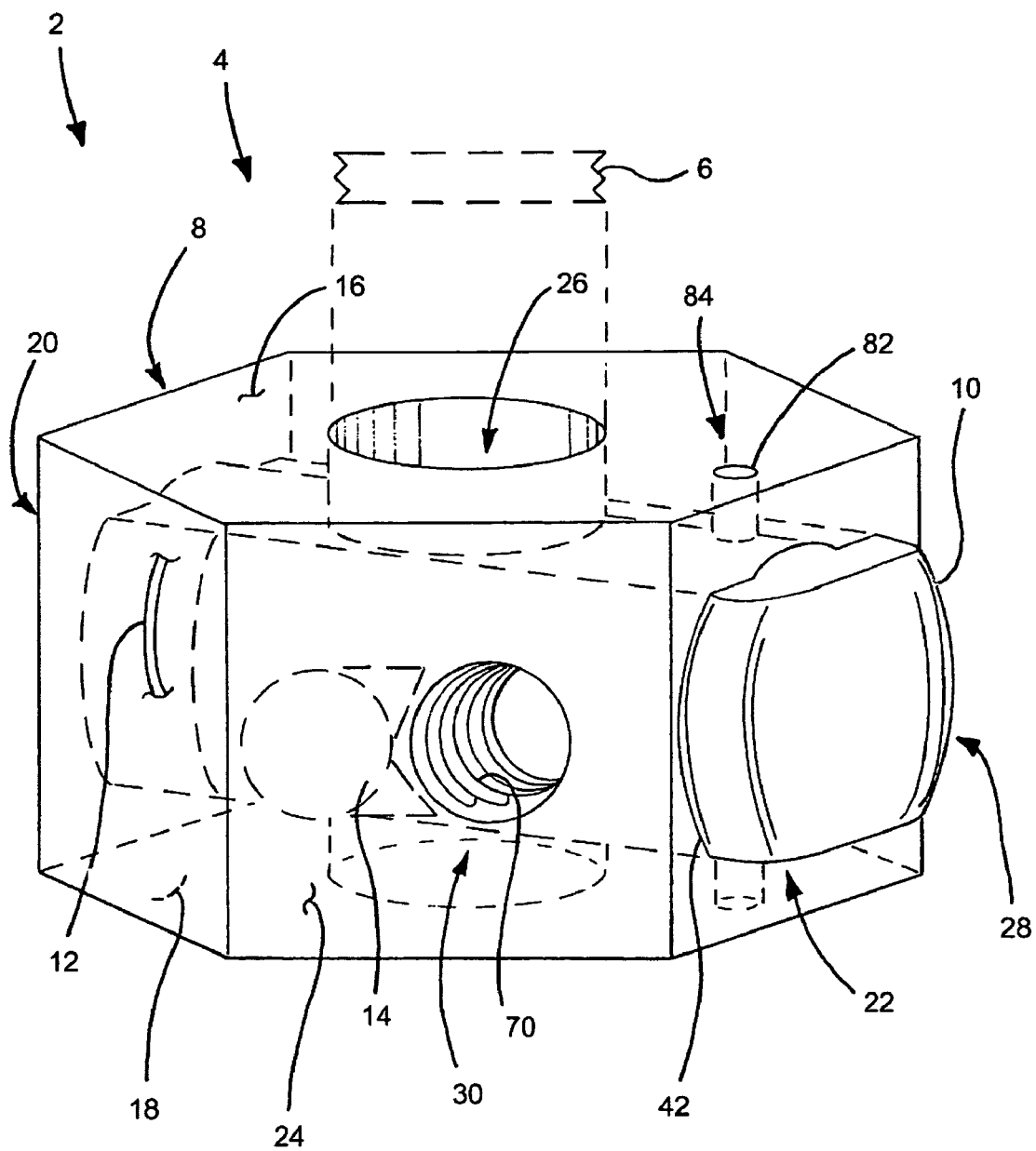
FIG. 1 depicts a perspective view of a nut of an assembly according to an embodiment of the present disclosure.

Embodiments of the present invention and the advantages thereof are best understood by referring to the following descriptions and drawings, wherein like numerals are used for like and corresponding parts of the drawings.

According to the present disclosure and referring now to FIGS. 1 through 4, an assembly 2 is shown. The assembly 2 includes a nut assembly 4. The nut assembly 4 cooperates with a fixation rod 6. The nut assembly 4 is utilized to move along the fixation rod 6 for use in an instrument, for example an orthopaedic external fixation device. The nut assembly 4 includes a body 8 and a plunger 10 that is slideably fitted to the body 8. The plunger 10 is threadably engageable with the rod 6.

The plunger 10 has a position in the body 8 in which the plunger 10 engages the fixation rod 6 to provide threaded cooperation between the nut assembly 4 and the fixation rod 6. The plunger 10 also has a second position in which the plunger 10 is spaced from the fixation rod 6. In this second position the nut assembly 4 may move freely axially along the fixation rod 6. The nut assembly 4 further includes an urging member 12 to urge the plunger 10 into engagement with the fixation rod 6. The assembly 2 further includes a lock member 14 that is configured to lock the plunger 10 into engagement with the fixation rod 6.

The body 8 has a first surface 16, a second surface 18, and a third surface 20. The third surface 20 extends between the first surface 16 and the second surface 18. The first surface 16 and second surface 18 are typically spaced from each other and, as is shown in FIG. 1, are parallel to each other and spaced from each other. The first surface 16 and the second surface 18 may be in the form of planer surfaces. The third surface 20 may have any suitable shape and may be in the form of a geometric or non-geometric surface. Preferably, the third surface 20 has a non-uniform shape or does not have a generally cylindrical shape. The non-uniform shape permits a tool (not shown) to engage with the third surface 20 to rotate the body 8. For example, the third surface 20 may be a polygon, for example, a rectangle or a hexagon. The third surface 20 is shown as a hexagonal surface. The third surface 20 includes a first facet 22 and a second facet 24.

The body 18 defines a first passageway 26 extending from the first surface 16 to the second surface 18 and a second passageway 28 extending from the third surface 20 to the first passageway 26. The body 8 further defines a third passageway 30 extending from the third surface 20. The third passageway 30 may extend to either the first passageway 26 or the second passageway 28. As is shown in FIG. 1, the second passageway 28 may pass through the first passageway 26 and the first passageway 26 may pass through the second passageway 28.

Continuing to refer to FIG. 1, the second passageway 28 extends from the first facet 22 of the third surface 20 to the first passageway 26. The third passageway 30 as shown in FIG. 1 extends from the second facet 24 to either the first passageway 26 or the second passageway 28. As described earlier, the first passageway 26 and the second passageway 28 may intersect, overlap, or be coexistent in a portion of the passageways 26 and 28.

Figure 5:
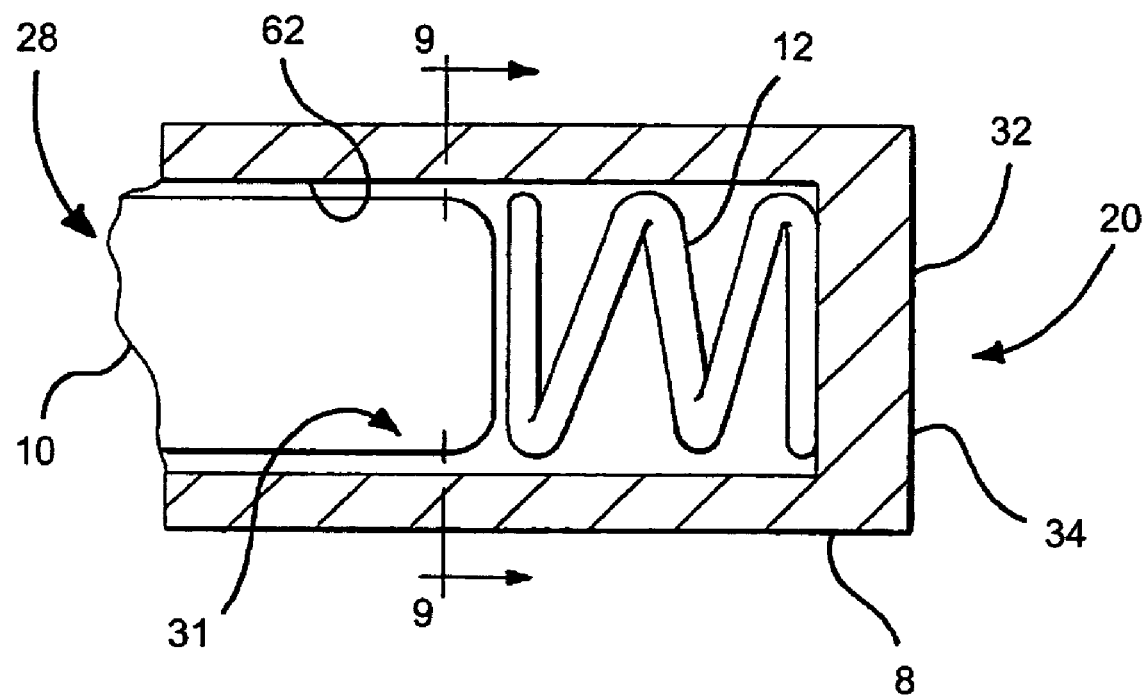
FIG. 5 depicts a partial cross sectional view of the spring of the nut of the assembly of FIG. 1 positioned in the second passageway of the body of the nut.
Figure 9:
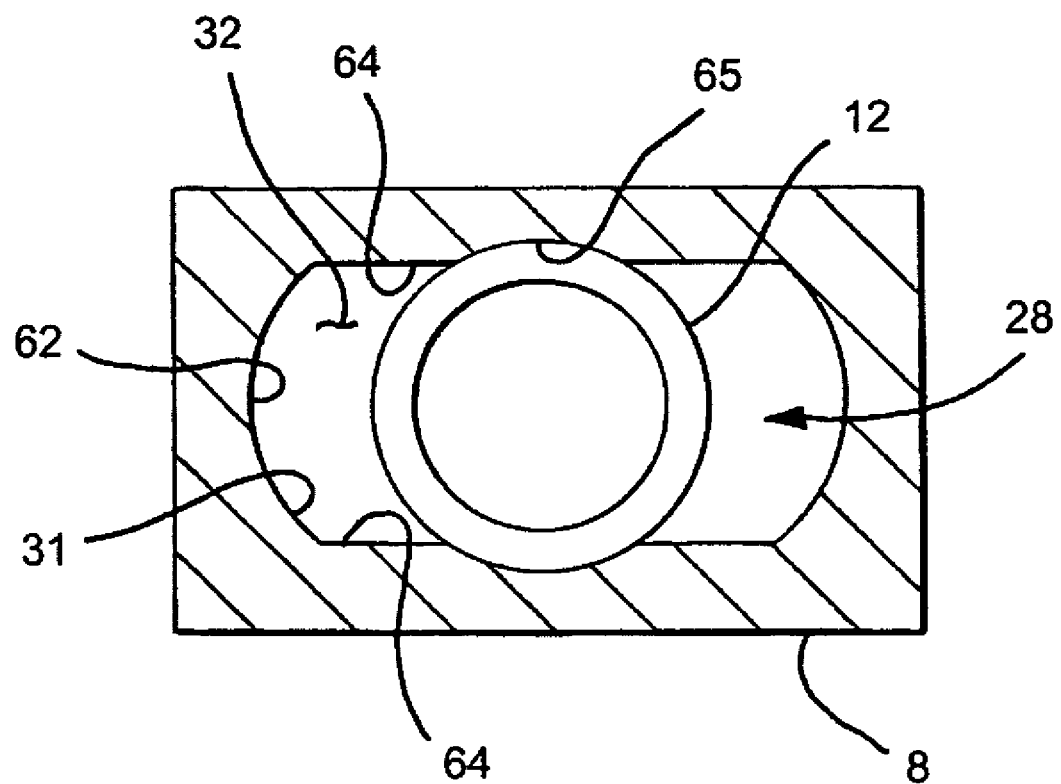
FIG. 9 depicts a cross sectional view of FIG. 5 along the line 9-9 in the direction of the arrows.

Referring now to FIGS. 5 and 9, the second passageway 28 includes a blind bore 31 which forms a pocket for receiving the biasing member 12. The pocket 31 has a closed end 32 which is adjacent third facet 34 of the third surface 20 of the body 8. The biasing member 12 is located within the pocket or blind bore 31 and between the closed end 32 of the blind bore 31 and the plunger 10.

The biasing member 12 may be any member capable of urging the plunger 10 into engagement with the fixation rod 6. For example the biasing member 12 may be in the form of a resilient material, for example a metal or a polymer, for example a natural rubber or a synthetic rubber. As shown in FIGS. 5 and 9, the biasing member 12 is in the form of a spring. The spring 12 may be a leaf spring or, as is shown in FIGS. 5 and 9, in the form of a coil spring. The coil spring 12 has a generally cylindrical shape and an outer periphery that closely conforms to arcuate portion 65 of sliding periphery 62 of the body 8.

Figure 6:
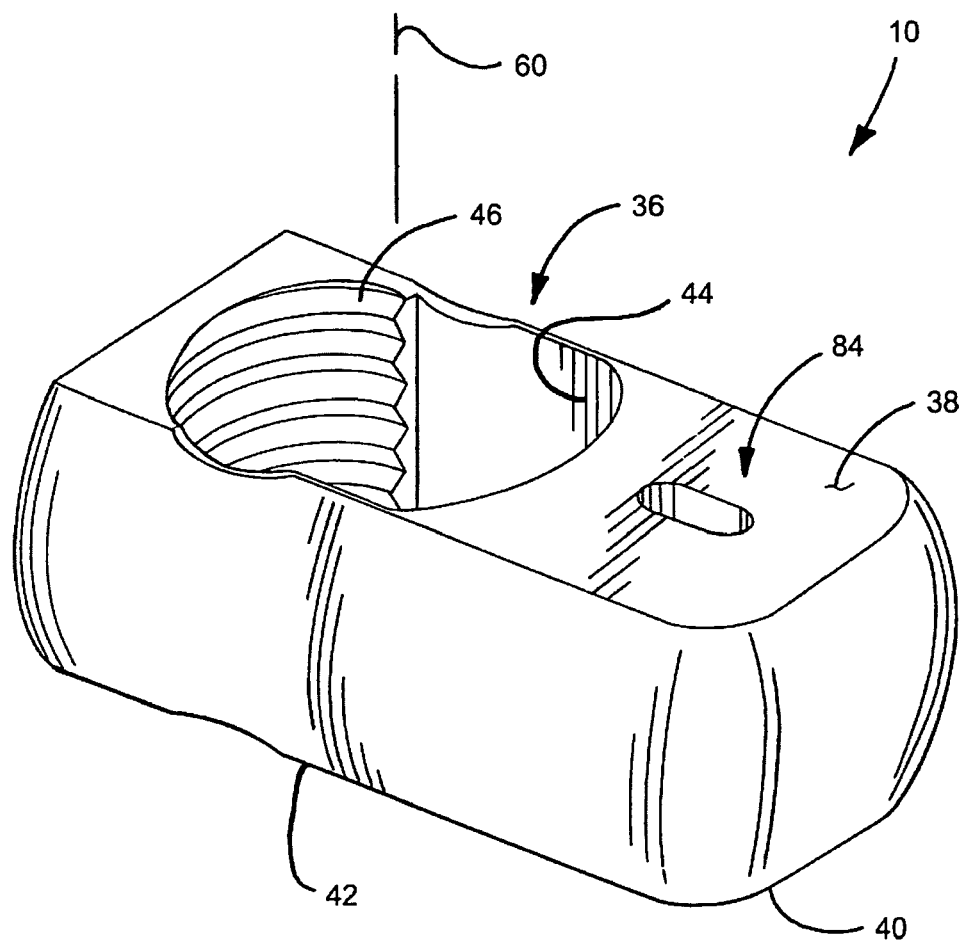
FIG. 6 depicts a perspective view of the plunger of the nut of the assembly of FIG. 1.

Referring now to FIG. 6, the plunger 10 is shown in greater detail. The plunger 10 has a channel 36 extending through the plunger 10. The plunger 10 may have any shape such that it is received within the second passageway 28 of the body 8 so that the plunger 10 may slide within the second passageway 26. The plunger 10 defines an interior surface 44 that forms the channel 36 and that has a threaded portion 46. The threaded portion 46 of the plunger 10 cooperates with the fixation rod 6 (see FIG. 1) to provide threaded engagement of the nut assembly 4 with the fixation rod 6 when the plunger 10 is in contact with the fixation rod 6.

As shown in FIG. 6, the plunger 10 includes first planar surface 38 and opposed second planer surface 40. The planar surfaces 38 and 40 are spaced from each other and may, as is shown in FIG. 6, be parallel to each other.

Figure 7:
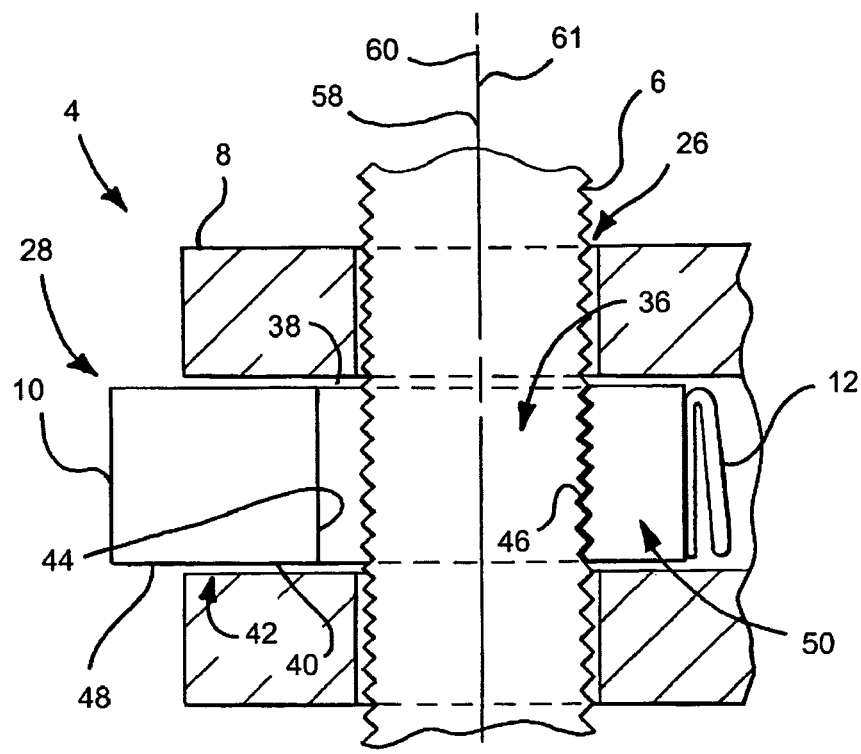
FIG. 7 depicts a partial cross sectional view of the nut of the assembly of FIG. 1 engaged with the rod of the distractor.
Figure 8:
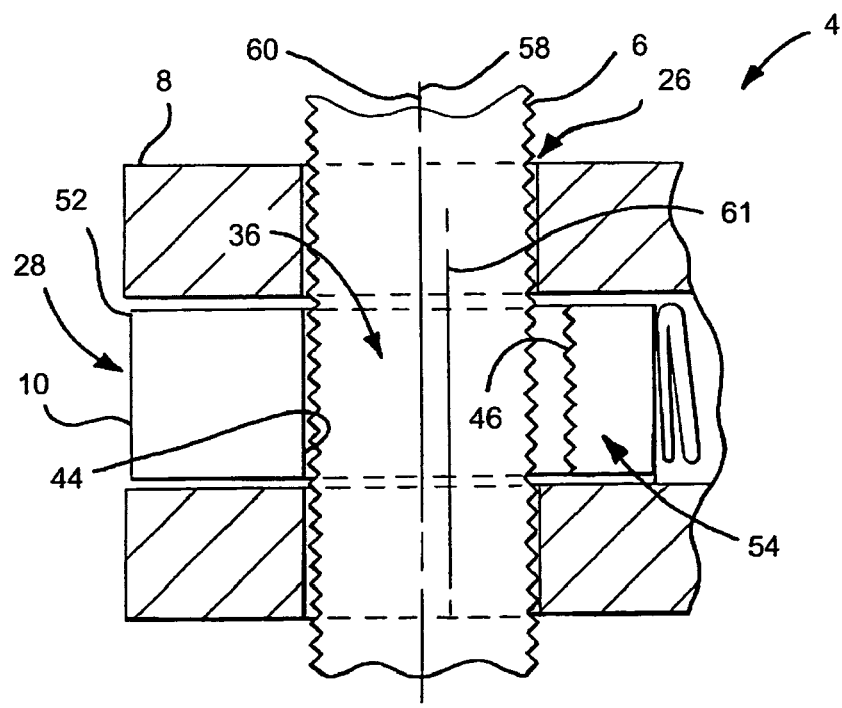
FIG. 8 depicts a partial cross sectional view of the nut disengaged from the rod of the distractor.

Referring now to FIGS. 7 and 8, the plunger 10 is positionable within the second passageway 28 at a first plunger position 48, as shown in FIG. 7, in which the threaded portion 46 of the interior surface 44 of the plunger 10 is located at a first location 50 with respect to the body 8. At the first location 50, the threaded portion 46 threadably engages the threaded rod 6.

Referring now to FIG. 8, the plunger 10 is moveable from the first plunger position to a second plunger position 52 in which the threaded portion 46 of the interior surface 44 of the plunger is located at a second location 54 with respect to the body 8. At the second location 54, the threaded portion 46 is spaced apart from the threaded rod 6.

The fixation rod 6 includes a longitudinal center line 58 and the channel 36 of the plunger 10 includes a channel longitudinal center line 61. The plunger 10 is moveable to the second plunger position 52 so that the center line 58 of the rod 6 is aligned or co-existent with center line 61 of the channel 36 of the plunger 10. In this aligned configuration the nut assembly 4 may be slideably moved along the center line 58 of the rod 6.

Referring again to FIG. 7, when the plunger 10 is positioned in the first plunger position 48 the threaded portion 46 of the plunger 10 engages the rod 6. In this first plunger position 48, the rotation of the body 8 in relation to the threaded fixation rod 6 causes the body 8 and correspondingly the nut assembly 4 to move along longitudinal centerline 58 of the threaded fixation rod 6.

Figure 2:
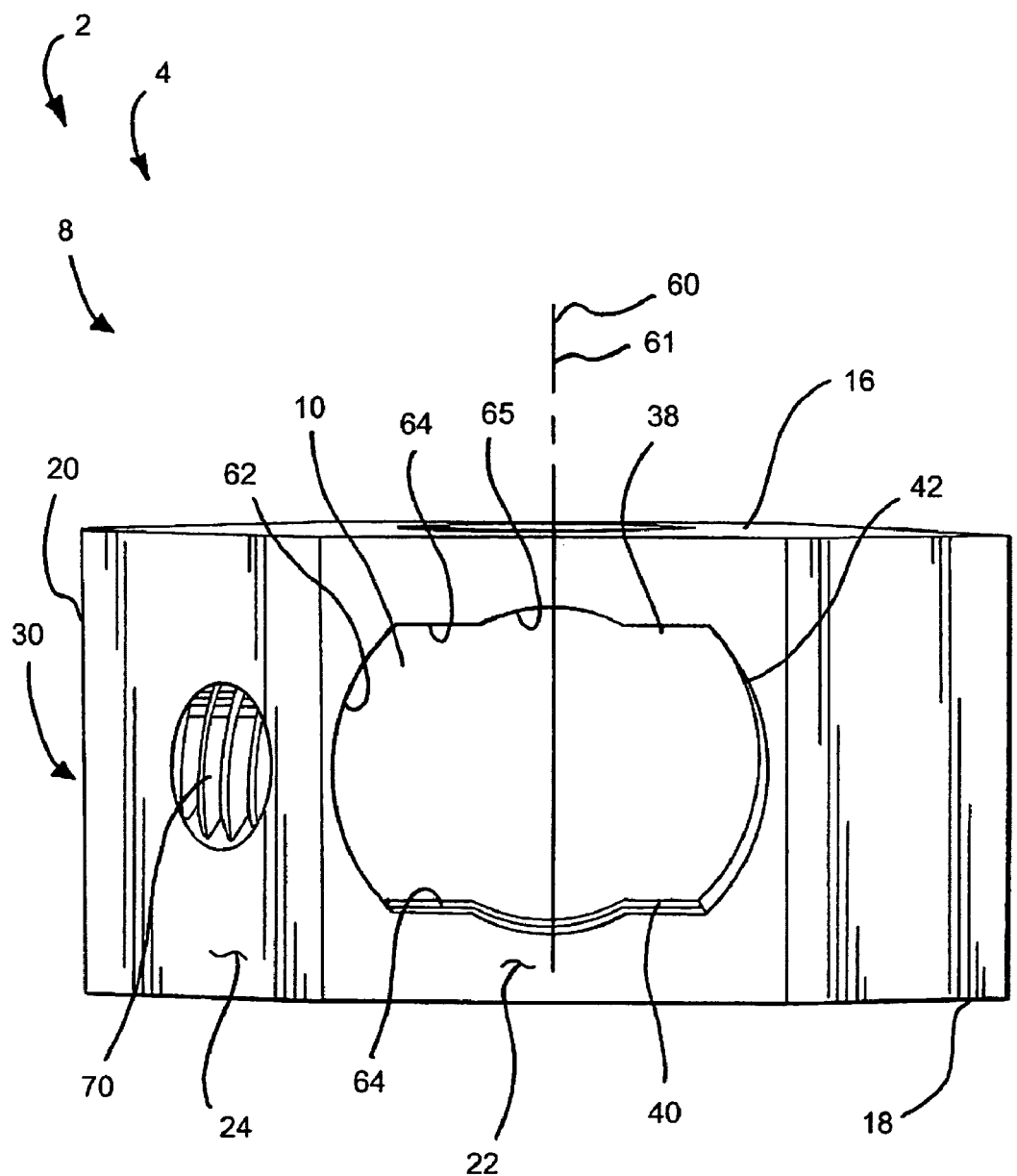
FIG. 2 depicts another perspective view of the nut of FIG. 1 showing the plunger in the plunger passageway and the threaded passageway for receiving the lock member.

Referring now to FIGS. 2 and 9, the second passageway 28 of the body 8 defines a periphery 62 including opposed flats 64. The flats 64 may be planar and may correspond to and slidingly mate against planar surfaces or flats 38 and 40 of the plunger 10. The flats 64 of body 8 cooperate with the flats 38 and 40 of plunger 10 to align the longitudinal centerline 61 of the channel 36 of the plunger 10 with longitudinal centerline 60 of the first passageway 26 of the body 8.

Figure 3:
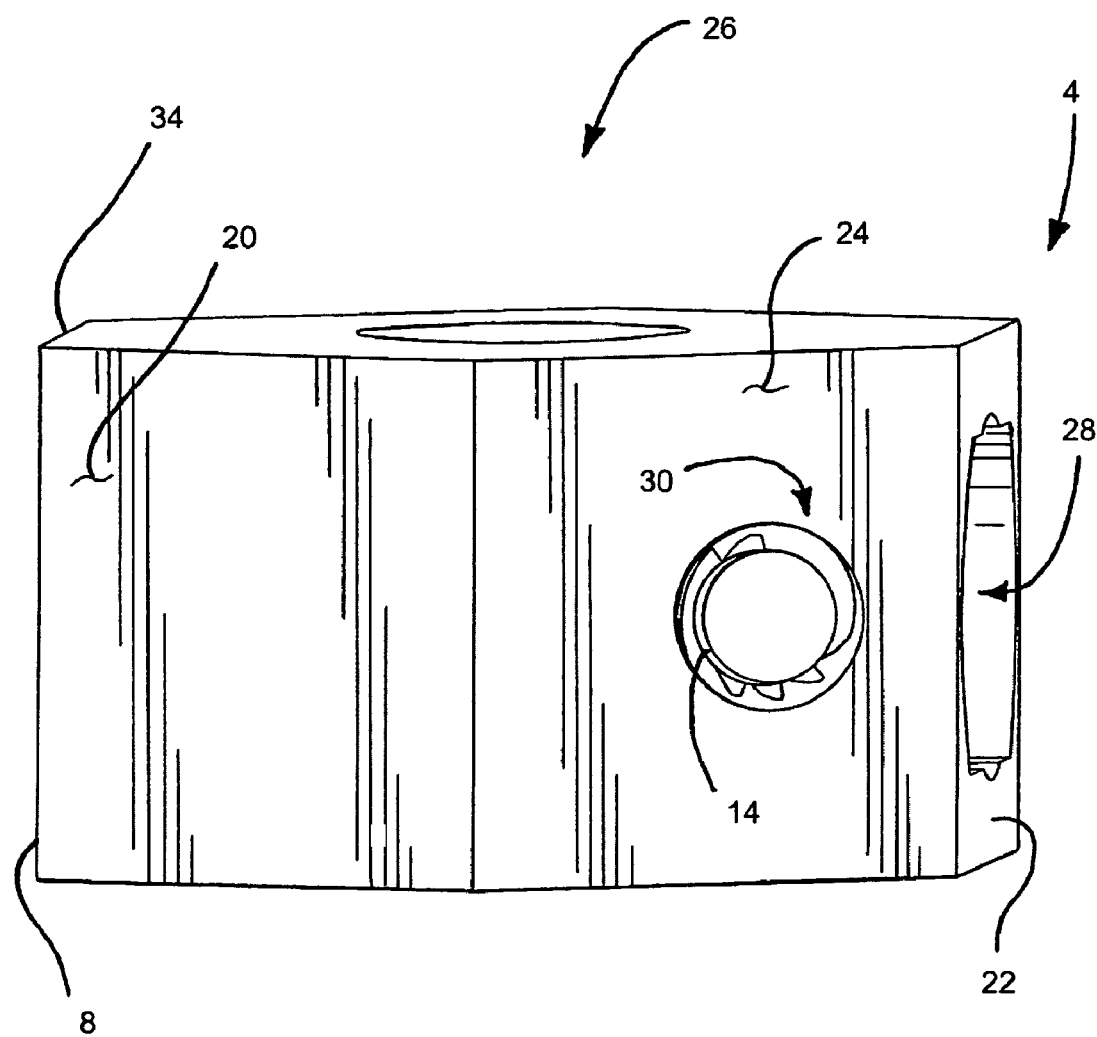
FIG. 3 depicts another perspective view of the nut of FIG. 1 showing the lock member in the lock member passageway and the plunger passageway.
Figure 10:
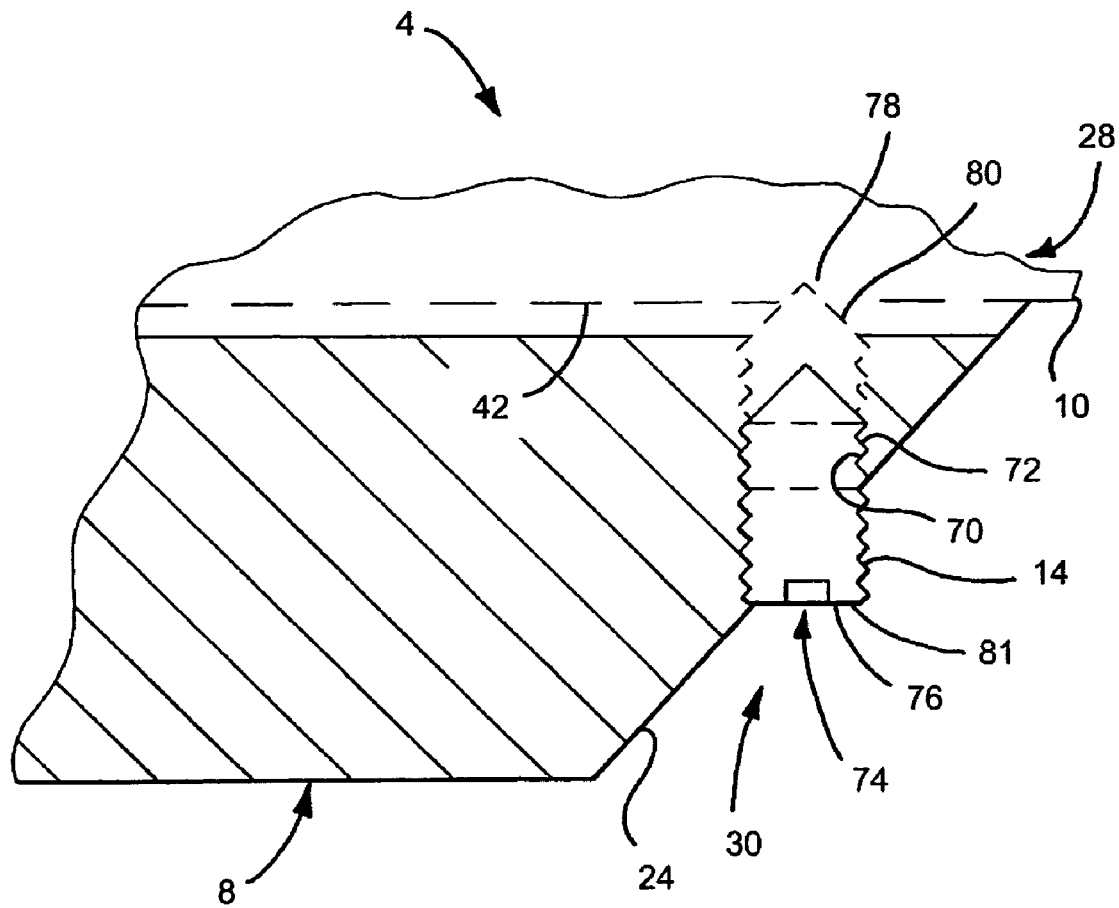
FIG. 10 depicts a partial cross sectional view of the set screw of the nut of the assembly of FIG. 1 spaced from the plunger in solid and engaged with the plunger in phantom.

Referring now to FIGS. 3 and 10, the lock member 14 is shown in greater detail. The lock member 14 may be any member capable of locking the plunger 10 to the body 8. For example, the lock member 14 may be a pin, a wedge or other mechanical structure that may be in physically contact with the body 8 and the plunger 10. As shown in FIGS. 3 and 10, the lock member 14 is in the form of a set screw. The set screw 14 is fitted to body 8 of the nut assembly 4. As shown in FIG. 2, the body 8 includes an interior threaded surface 70 that defines the third passageway 30.

Referring now to FIG. 10, the set screw 14 includes an exterior threaded surface 72 that is meshingly engaged with the interior threaded surface 70 of the body 8. The set screw 14 is movable within the third passageway 30 between a first lock member position 80 as shown in phantom in FIG. 10 in which the set screw 14 inhibits movement of the plunger 10 within the second passageway 28 and a second lock member position 81 as shown in solid in which the set screw 14 allows movement of the plunger 10 within the second passageway 28.

The set screw 14 may be any suitable set screw and may include an engaging feature 74 that cooperates with a tightening tool (not shown). The tool rotates the set screw 14 with respect to the interior threaded surface 70 of the body 8 to selectively engage the set screw 14 against the plunger 10 and to selectively release the set screw 14 from the plunger 10. The engaging feature 74 may be in the form of an interior or exterior geometric or non-geometric feature.

Preferably the engaging feature 74 is other than a cylindrical surface such that torque may easily be applied to the set screw 14 by the tightening tool. For example, the engaging feature may be defined by a hexagonal-shaped recess. The set screw 14 includes a head 76 which includes the engaging feature 74. The head 76 is recessed or positioned below second facet 24 of the third surface 20 of the body 8. By positioning the head 76 below the second facet 24, access to the head 76 and the engaging feature 74 is reduced so that the set screw 14 may not be inadvertently loosened.

The set screw 14 further includes a plunger-engaging surface 78 opposed to the engaging feature 74. The plunger-engaging surface 78 may have a point contact or an area contact. If the plunger-engaging surface 78 has a point contact, the plunger-engaging surface 78 may, for example, have a conical shape. If the plunger-engaging surface 78 is a flat surface, the surface 78 may have, for example, a circular ring contact surface or a flat cylindrical surface.

Figure 4:
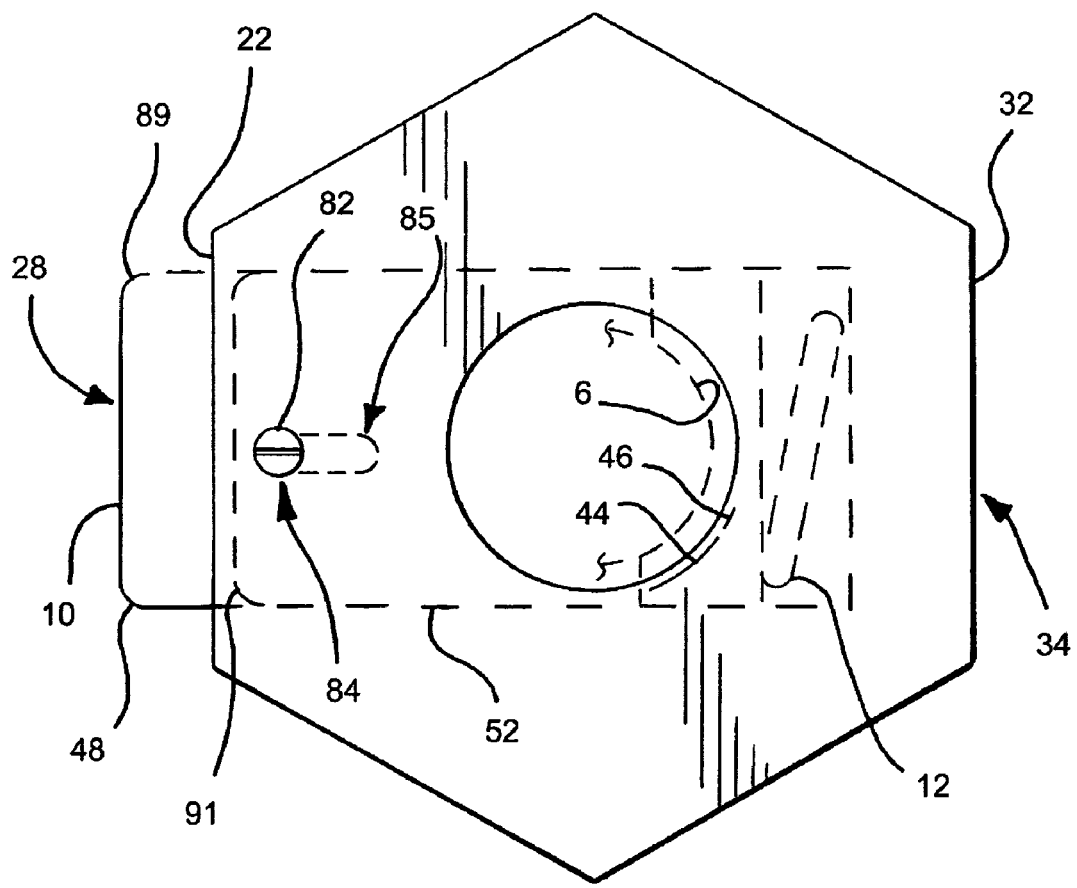
FIG. 4 depicts a top view of the nut of the assembly of FIG. 1.

Referring now to FIGS. 1, 4 and 6, the assembly 2, which includes the nut assembly 4, further includes a retainer 82. The retainer 82 serves to retain the plunger 10 within the body 8. It should be appreciated that the retainer 18 may be any component that may be utilized to retain the plunger 8. For example, the retainer 82 may be a fastener, a wedge, or a protrusion.

As shown in FIGS. 1, 4 and 6, the retainer 82 is in the form of a pin. The pin 82 may have any suitable shape and for simplicity is a cylindrical pin. It should be appreciated that the pin 82 may be a solid cylindrical pin or may be in the form of a roll pin. The body 8, as shown in FIG. 4, further has a first retainer passageway 84 defined in the body 8. As shown in FIG. 1, the first retainer passageway 84 extends completely from bottom surface 18 to top surface 16 of the body 8. It should be appreciated that alternatively the first retainer passageway 84 may merely extend from either the first surface 16 or the second surface 18 as long as the first retainer passageway 84 passes into the second passageway 28 of the body 8 so that the retainer 82 may engage the plunger 10.

Referring again to FIG. 4, the plunger 10 further has a second retainer passage 85 defined in the plunger 10. As shown in FIG. 4, the second retainer passage 85 extends from first planar surface 38 of the plunger 10 through second planar surface 40 of the plunger 10. It should be appreciated that alternatively the second retainer passage 85 may extend only partially below the first planar surface 38 to engage the retainer 82. The retainer 82 is positioned in both the first retainer passage 84 and the second retainer passage 85.

Referring again to FIG. 4, movement of the plunger 10 within the second passageway 28 causes movement of the plunger 10 in relation to the retainer 82. Such movement of the plunger 10 within the second passageway 28 is accomplished by providing the second retainer passageway 85 in the form of an elongated slot. By providing an elongated slot, the retainer 82 may cooperate with the slot 85 to provide a first non-engaged passageway position 89, as shown in solid, in which the fixation rod 6 is spaced from threaded portion 46 of the inner surface 44 of the plunger 10 and a second engaged passageway position 91, as shown in phantom in FIG. 4, in which the threaded rod 6 is engaged with the threaded portion 46 of the interior surface 44 of the plunger 10.

Figure 11:
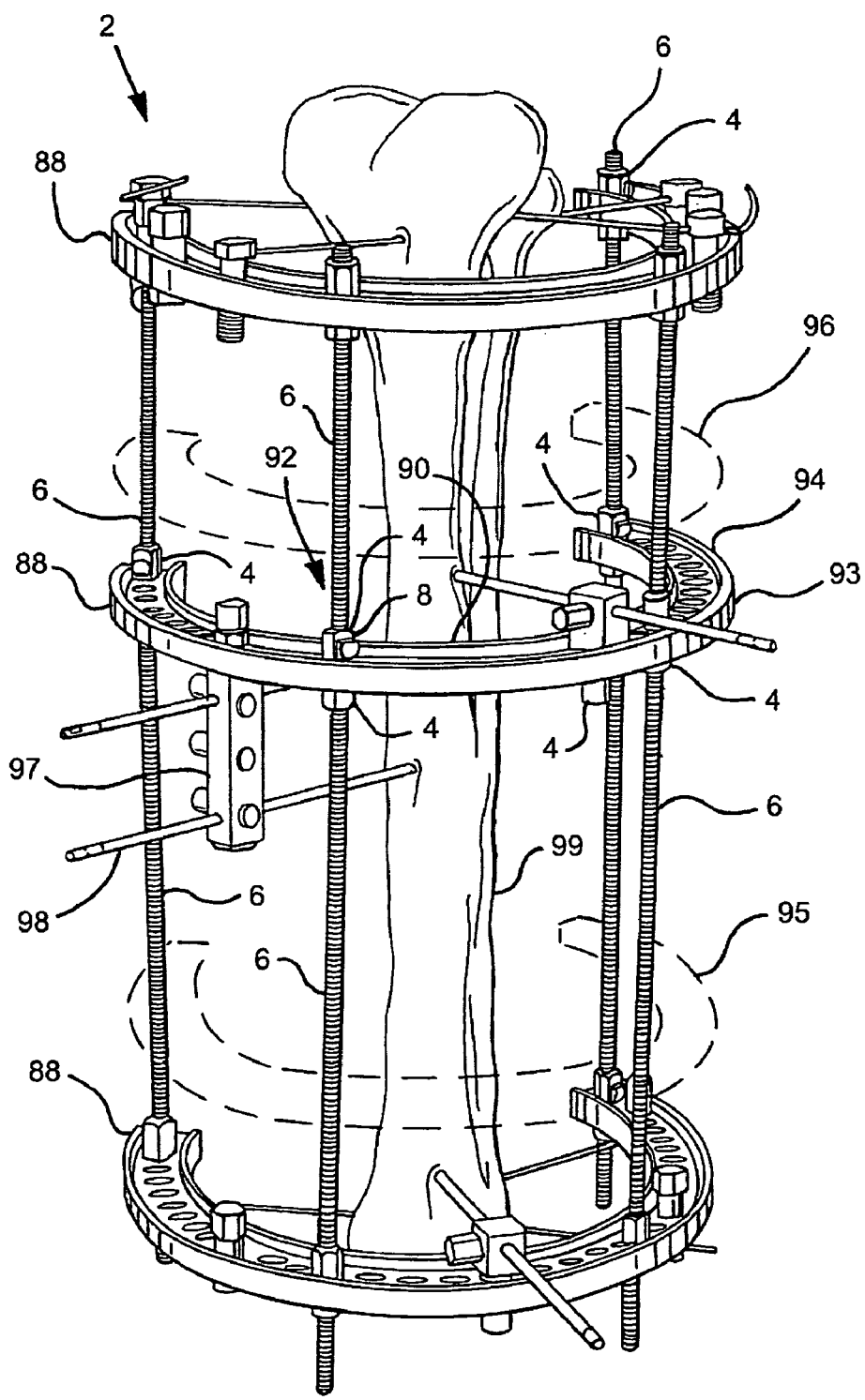
FIG. 11 depicts a perspective view of an assembly according to an embodiment of the present disclosure in the form of an external fixator implanted on a tibia of a patient including rings and distractors using the nut of the assembly of FIG. 1.
Figure 12:
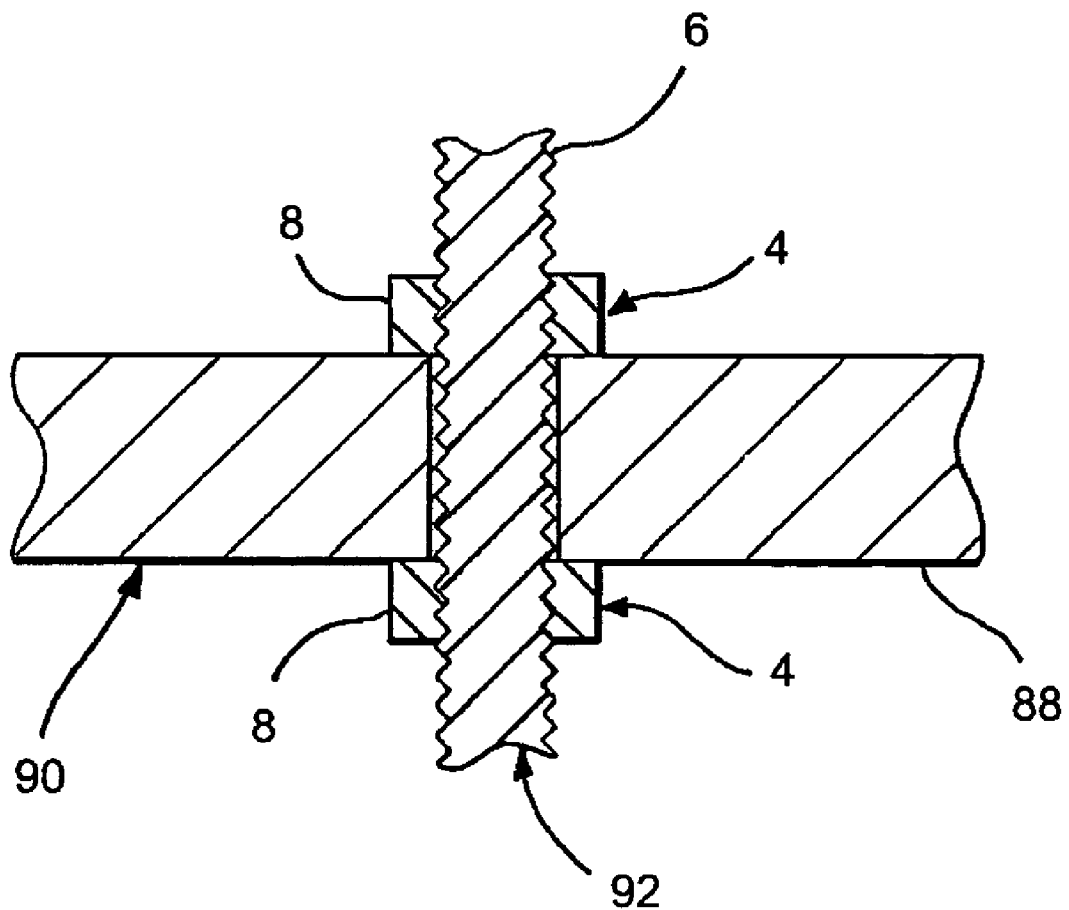
FIG. 12 depicts a partial plan view of the nut of the assembly of FIG. 1 engaged with the distractor and ring of the external fixator of FIG. 1.

Referring now to FIGS. 11 and 12, the assembly 2 of the present disclosure further includes a fixation member 88. The fixation member 88 includes at least one arcuate portion 90 having a hole 92 extending through the arcuate portion 90. The threaded fixation rod 6 extends through the hole 92 of the arcuate portion 90.

Referring now to FIG. 12, the body 8 of the nut assembly 4 is shown in contact with fixation member 88. The fixation rod 6 threadably engages with the nut assembly 4 to secure the fixation rod 6 to the fixation member 88. It should be appreciated that the fixation member 88, to be fixedly positioned to the fixation rod 6, either needs to have the body 8 of the nut assembly 4 physically secured to the fixation member 88 or, as shown in FIG. 12, needs to have a second nut assembly 4 positioned on the threaded fixation rod 6 in a position against the fixation member opposed to the first nut assembly 4. In this configuration the arcuate portion of the fixation member 88 is sandwiched or positioned between opposed nut assemblies 4. By threadably engaging the nut assemblies 4 to the fixation member 88, the fixation member 88 may be rigidly secured to the fixation rod 6, as shown in FIG. 12.

Referring again to FIG. 11, the assembly 2 of the present disclosure may have a solitary fixation member 88 secured to a fixation rod 6 by nut assembly 4 to form assembly 2. Typically, however, to utilize the fixation member 88 and the assembly 2 to reduce a fracture of bone 99, the assembly 2 includes, in addition to the first fixation member 88, a separate second spaced apart fixation member 88. A third spaced apart fixation member 88 may also be used. The second fixation member 88 may be in the form of a central fixation member 93. The central fixation member 93 may be movable with respect to the opposing end fixation members 88. By providing a central fixation member 93 that may be slideably moved along the threaded fixation rods 6, the bone 99 may be engaged at a proper location. For example, and as shown in FIG. 11, the assembly 2 includes the central ring 93 positioned between the opposed end fixation members 88.

While the fixation members 88 may cooperate with a solitary threaded fixation rod 6, as shown in FIG. 11, a plurality of fixation rods 6 are used to provide for a rigid assembly. The assembly 2 of FIG. 11, for example, includes four spaced-apart threaded fixation rods 6. As shown in FIG. 11, each of the threaded fixation rods 6 are fitted in holes 92 formed in the fixation members 88. Each of the fixation members 88 includes four holes 92 to receive the appropriate one of the four fixation rods 6.

The assembly 2, as shown in FIG. 11, further includes brackets 97 that mount to one of the fixation members 88 and receive pins 98 that are slidingly engageable with the brackets 97 to be advanced toward bone 99 to rigidly engage with the bone 99. It should be appreciated that the pins 98 may engage the external cortex of the bone 98 or extend into the cancellous bone or alternatively extend completely through the bone 99. A plurality of pins 98 may be attached to a particular bracket 97.

The nut assembly 4 including the body 8, the retainer 82, the set screw 14, the plunger 10, and the spring 12 may be made of any suitable durable material that may be sterilized by any known sterilization technique. For example these components may be made of a metal, a polymer, or a composite material. If made of a metal, these components may be, for example, made of cobalt chromium alloy, stainless steel alloy, or a titanium alloy. The components may all be made of the same material to avoid any issues due to the use of dissimilar materials. The rings 88, the pins 98, the rod 6, and the bracket 97 may be made of any suitable durable material that may be sterilized and may be made of the materials discussed above relative to the nut assembly 4.

As shown in FIG. 11, the central ring 93 cooperates with eight nut assemblies 4, with two of the eight nut assemblies 4 associated with each of the four fixation rods 6. The central ring 93 may be moved from first position 94, as shown in solid, by first threadably loosing the nut assembly 4 from the ring 93 and then depressing the plunger 10 of the nut assemblies 4 to separate the threaded portion 46 of the plunger 10 from the threaded fixation rods 6. The nut assemblies 4 and the central ring 93 may then be moved axially along the fixation rods 6. For example, initially the four lower nut assemblies 4 are threadably released from the rods 6 and moved along the fixation rods 6. The central ring 93 may then be moved from its central position 94 as shown in solid to the lower position 95 as shown in phantom. After the central ring 93 is moved to the lower position 95, the four upper nut assemblies 4 may be released by depressing the plunger 10 and slidingly moving them downwardly into contact with the ring 93. At this point, a fastener, for example an open-end wrench, may be used to threadably tighten the nut assemblies 4 rigidly against the central ring 93. After each of the eight nut sd assemblies 4 are tightened against the central ring 93 by the open-end wrench, the nut assemblies 4 are locked by utilizing a set screw wrench (not shown) to tighten the set screws 14 threadably engaged to the body 8 against the plunger 10 to lock the threaded portion 46 of the plunger 10 into engagement with the external threads on the fixation rods 6.

Similarly, the center ring 93 may be moved upwardly to third position 96 as shown in dotted line. It should be further appreciated that the upper fixation member 88 and the lower fixation member 98 may likewise be movable. For simplicity and to reduce cost, the upper and lower rings 88 may be tightened by regular hexagonal nuts and the center ring 93 may be utilized with the nut assemblies 4 of the present disclosure in that the center ring 93 is more likely to need to be adjusted to position it adjacent the fracture.

It should be appreciated that merely two rings 88 may be utilized and likewise four or more rings 88 may be utilized in the assembly 2 of the present disclosure. As shown, the fixation members 88 have an arcuate form and extend partially around the bone 88. It should be appreciated that alternatively the fixation members 88 may be a full circular ring. If a full circular ring, the ring may include two halves that have an open position to receive the bone. After receiving the bone, the two halves are closed to form the full circular ring.

Of course, numerous other adaptations are possible. Moreover, there are advantages to individual advancements described herein that may be obtained without incorporating other aspects described above. Therefore, the spirit and scope of the appended claims should not be limited to the description of the preferred embodiments contained herein.

We claim:

1. An assembly, comprising:
   a body having a top surface, a bottom surface, and a polygonal drive surface interposed between said top surface and said bottom surface, said body defining (i) a first passageway extending from said top surface to said bottom surface, (ii) a second passageway extending from said polygonal drive surface to said first passageway, and (iii) a third passageway extending from said polygonal drive surface to one of said first passageway and said second passageway;
   a plunger having channel extending therethrough that defines an interior surface having a threaded portion, said plunger being movable within said second passageway between (i) a first plunger position in which said threaded portion is located at a first location with respect to said body, and (ii) a second plunger position in which said threaded portion is located at a second location with respect to said body;
   a biasing member configured to bias said plunger toward said first plunger position, and
   a set screw that is movable within said third passageway between (i) a first set screw position in which said set screw inhibits movement of said plunger within said second passageway, and (ii) a second set screw position in which said set screw allows movement of said plunger within said second passageway.

2. The assembly of claim 1, further comprising a retainer, wherein:
   said body further has a first retainer passage defined therein,
   said plunger further has a second retainer passage defined therein,
   said retainer is positioned in both said first retainer passage and said second retainer passage, and
   movement of said plunger within said second passageway causes movement of said plunger in relation to said retainer.

3. The assembly of claim 2, wherein said retainer includes a pin positioned within both said first retainer passage and said second retainer passage.

4. The assembly of claim 1, wherein said polygonal drive surface is a hexagonal drive surface.

5. The assembly of claim 1, wherein:
   said top surface lies in a first plane, said bottom surface lies in a second plane, and
said first plane is parallel to said second plane.

6. The assembly of claim 1, wherein:
said second passageway includes a blind bore having a closed end, and
said biasing member is located within said blind bore and adjacent to said closed end.

7. The assembly of claim 1, wherein said threaded portion of said plunger includes a plurality of partial threads defined on said interior surface of said plunger.

8. The assembly of claim 1, further comprising a threaded fixation rod extending through said first passageway, wherein:
said threaded portion of said plunger is spaced apart from said threaded fixation rod when said plunger is located in said second plunger position, and
said threaded portion of said plunger is positioned in meshing relationship with said threaded fixation rod when said plunger is positioned in said first plunger position.

9. The assembly of claim 8, wherein when said plunger is positioned in said first plunger position, rotation of said body in relation to said threaded fixation rod causes movement of said body along an axis of said threaded fixation rod.

10. The assembly of claim 8, further comprising a fixation member, wherein:
said fixation member includes, at least, an arcuate portion having a hole extending therethrough,
said threaded fixation rod extends through said hole of said arcuate portion, and
said body is positioned in contact with said arcuate portion.

11. The assembly of claim 1, wherein:
said polygonal drive surface includes a first facet and a second facet,
said second passageway extends from said first facet to said first passageway, and
said third passageway extends from said second facet to one of said first passageway and said second passageway.

12. The assembly of claim 1, wherein:
said body includes an interior threaded surface that defines said third passageway, and
said set screw includes an exterior threaded surface that is meshingly engaged with said interior threaded surface.

13. The assembly of claim 1, wherein said biasing member is a spring located within said second passageway.

14. An assembly, comprising:
a body having a first surface, a second surface, and a third surface extending between said first surface and said second surface, said body defining (i) a first passageway extending from said first surface to said second surface, (ii) a second passageway extending from said third surface to said first passageway, and (iii) a third passageway extending from said third surface to one of said first passageway and said second passageway;
a plunger having channel extending therethrough that defines an interior surface having a threaded portion, said plunger being movable within said second passageway between (i) a first plunger position in which said threaded portion is located at a first location with respect to said body, and (ii) a second plunger position in which said threaded portion is located at a second location with respect to said body;
a biasing member configured to bias said plunger toward said first plunger position, and
a lock member that is movable within said third passageway between (i) a first lock member position in which said lock member inhibits movement of said plunger within said second passageway, and (ii) a second lock member position in which said lock member allows movement of said plunger within said second passageway.

15. The assembly of claim 14, further comprising a pin, wherein:
said body further has a first pin passage defined therein,
said plunger further has a second pin passage defined therein,
said pin is positioned in both said first pin passage and said second pin passage, and
movement of said plunger within said second passageway causes movement of said plunger in relation to said pin.

16. The assembly of claim 14, wherein:
said third surface is a polygonal drive surface,
said polygonal drive surface includes a first facet and a second facet,
said second passageway extends from said first facet to said first passageway, and
said third passageway extends from said second facet to one of said first passageway and said second passageway.

17. The assembly of claim 14, wherein:
said first surface lies in a first plane,
said second surface lies in a second plane, and
said first plane is parallel to said second plane.

18. The assembly of claim 14, wherein:
said second passageway includes a blind bore having a closed end, and
said biasing member is located within said blind bore and adjacent to said closed end.

19. The assembly of claim 14, wherein said threaded portion of said plunger includes a plurality of partial threads defined on said interior surface of said plunger.

20. The assembly of claim 14, further comprising a threaded fixation rod extending through said first passageway, wherein:
said threaded portion of said plunger is spaced apart from said threaded fixation rod when said plunger is located in said second plunger position, and
said threaded portion of said plunger is positioned in contact with said threaded fixation rod when said plunger is positioned in said first plunger position.

21. The assembly of claim 20, further comprising a fixation member, wherein:
said fixation member includes, at least, an arcuate portion having a hole extending therethrough,
said threaded fixation rod extends through said hole of said arcuate portion, and
said body is positioned in contact with said arcuate portion.

22. The assembly of claim 14, wherein:
said body includes an interior threaded surface that defines said third passageway, and
said lock member includes an exterior threaded surface that is meshingly engaged with said interior threaded surface.

* * * * *

UNITED STATES PATENT AND TRADEMARK OFFICE
CERTIFICATE OF CORRECTION

PATENT NO.         : 8,002,773 B2
APPLICATION NO.    : 12/214168
DATED              : June 17, 2008
INVENTOR(S)        : Clinton E. Kehres It is certified that error appears in the above-identified patent and that said Letters Patent is hereby corrected as shown below:

Column 2,
Line 63, replace "nut." with --nut;--

Column 3,
Line 7, replace "phantom." with --phantom;--

Column 3,
Line 15, replace "of FIG. 1;" with --of FIG. 1.--

Column 5,
Line 21, replace "in physically contact" with --in physical contact--

Column 7,
Line 60, before "assemblies 4" delete "sd"

Signed and Sealed this
Fifth Day of March, 2013

Teresa Stanek Rea
*Acting Director of the United States Patent and Trademark Office*